US008128591B2

(12) United States Patent
Simonton et al.

(10) Patent No.: US 8,128,591 B2
(45) Date of Patent: Mar. 6, 2012

(54) MULTIPLE COMPONENT MIXING AND DELIVERY SYSTEM

(75) Inventors: Thomas A. Simonton, Memphis, TN (US); Sean M. Haddock, Memphis, TN (US); Lehmann K. Li, Milford, CT (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 24 days.

(21) Appl. No.: 12/268,075

(22) Filed: Nov. 10, 2008

(65) Prior Publication Data

US 2010/0121310 A1 May 13, 2010

(51) Int. Cl.
*A61M 37/00* (2006.01)

(52) U.S. Cl. .......................................... 604/82; 604/191

(58) Field of Classification Search .................... 604/82, 604/83–88, 89–92, 191
See application file for complete search history.

(56) References Cited

U.S. PATENT DOCUMENTS 3,764,229 A * 10/1973 Ferris et al. .................. 416/114
3,794,221 A 2/1974 Hostettler et al.
4,463,875 A * 8/1984 Tepic ............................ 222/82
4,676,406 A * 6/1987 Frischmann et al. ......... 222/136
4,676,655 A 6/1987 Handler
4,834,714 A 5/1989 Lascar et al.
5,100,241 A 3/1992 Chan
5,122,117 A * 6/1992 Haber et al. .................... 604/90
5,352,196 A * 10/1994 Haber et al. .................... 604/90
5,514,091 A 5/1996 Yoon
5,551,778 A 9/1996 Hauke
5,656,013 A 8/1997 Yoon
5,934,803 A * 8/1999 Hutter ........................... 366/139
6,183,518 B1 2/2001 Ross et al.
6,422,737 B1 7/2002 Welker
6,436,143 B1 8/2002 Ross et al.
6,458,096 B1 10/2002 Briscoe et al.
6,749,584 B2 6/2004 Briggs et al.
6,865,802 B2 3/2005 Lenzen et al.
6,932,843 B2 8/2005 Smith et al.
7,001,431 B2 2/2006 Bao et al.
7,018,089 B2 3/2006 Wenz et al.
(Continued)

FOREIGN PATENT DOCUMENTS

WO 2004026377 A1 4/2004
(Continued)

OTHER PUBLICATIONS

Innovations: "Dispensing cartridge mixes adhesives and other compounds," Medical Design; Sep. 2008; pp. 38.
(Continued)

*Primary Examiner* — Kevin C Sirmons
*Assistant Examiner* — Brandy C Scott

(57) ABSTRACT

A multiple component cartridge includes a barrel defining a chamber and a longitudinal axis. A first plunger is disposed within the chamber and in sealing engagement with the barrel. The first plunger includes at least one member and is movable relative to the barrel such that the at least one member is configured for movement relative to the first plunger to facilitate passage of at least a first component through the first plunger. A second plunger is disposed within the chamber and in sealing engagement with the barrel. The second plunger includes at least one member and is movable relative to the barrel such that the at least one member of the second plunger is configured for movement relative to the second plunger to facilitate passage of at least a second component through the second plunger.

16 Claims, 4 Drawing Sheets

U.S. PATENT DOCUMENTS

| | | | | |
|---|---|---|---|---|
| 7,144,386 | B2 | 12/2006 | Korkor et al. | |
| 7,247,149 | B2 | 7/2007 | Beyerlein | |
| 2004/0122359 | A1 * | 6/2004 | Wenz et al. | 604/82 |
| 2005/0119610 | A1 * | 6/2005 | Peuker et al. | 604/82 |
| 2007/0173943 | A1 | 7/2007 | Dulak et al. | |
| 2007/0255200 | A1 * | 11/2007 | McLean et al. | 604/82 |
| 2008/0025140 | A1 * | 1/2008 | Henniges et al. | 366/77 |

FOREIGN PATENT DOCUMENTS

| | | | |
|---|---|---|---|
| WO | 2004028440 | A2 | 4/2004 |

OTHER PUBLICATIONS

International Search Report and Written Opinion for US Application PCT/US2009/063406 mailed May 3, 2010.

* cited by examiner

1/4

MULTIPLE COMPONENT MIXING AND DELIVERY SYSTEM

TECHNICAL FIELD

The present disclosure generally relates to cartridges for storing, mixing and dispensing a multiple component mixture and more particularly to a multiple component cartridge having plungers with relatively movable members configured to facilitate mixing and delivery of a mixture, and related methods.

BACKGROUND

In many medical and dental procedures, it is required to mix components of a medical preparation just prior to application or delivery of the preparation. These preparations can include fluent components and solid components, such as a powder. Typically, these components react in some manner or cannot maintain consistency such that the components must be stored separately prior to mixing and delivery. Such separate storage also maintains sterilization. Further, it is often the case during a treatment procedure that the components are required to be mixed rapidly for effective delivery of the application.

Various mixing containers such as syringes and related apparatus are known for mixing two components for a medical preparation. These syringes separately store the components and rely on shaking or vibrating for mixing. Other syringes employ external mixing devices, such as a syringe for separately storing two components, which are separately dispensed into an external mixing nozzle. These type mixing containers can suffer from drawbacks such as difficulty of use and unreliable mixing during a medical procedure.

Various attempts have been made to overcome the disadvantages and drawbacks of the prior art. For example, a two component mixing device is known that has a plunger type mixing rod with a reduced diameter section that facilitates mixing. See, for example, U.S. Pat. No. 7,018,089. These devices may not facilitate mixing of two or more components or provide a desired agitation for mixing the components.

Therefore, it would be desirable to provide a multiple component mixing and delivering system, for storage, mixing, and delivery of multiple components for a medical treatment and related methods of use. Desirably, the multiple component cartridge includes plungers with relatively movable members configured to facilitate mixing and delivery of a multiple component mixture. It would be highly desirable if the multiple component cartridge provides a single device for mixing two or more, preferably three, separately stored components that can be delivered during a medical procedure. It is envisioned that the elements of the multiple component mixing and delivery system can be easily and efficiently manufactured and assembled.

SUMMARY OF THE INVENTION

Accordingly, a multiple component mixing and delivery system is provided, which includes a multiple component cartridge for storing, mixing, and delivering multiple components for a medical treatment, and related methods of use. Desirably, the multiple component cartridge includes plungers with relatively movable members configured to facilitate mixing and delivery of a multiple component mixture. Most desirably, the multiple component cartridge provides a single device for mixing two or more, preferably three separately stored components that can be delivered during a medical procedure. It is contemplated that the multiple component mixing and delivery system is easily and efficiently manufactured and assembled.

In one particular embodiment in accordance with the principles of the present disclosure, a multiple component mixing and delivery system is provided. The multiple component mixing and delivery system includes a cartridge having a barrel defining a chamber and a longitudinal axis. A first plunger is disposed within the chamber. In one embodiment the first plunger may include an elastomeric element, such as an O-ring, X-ring, or square-cut, around a perimeter of the first plunger, which forms a seal with the chamber. The first plunger includes at least one member configured for movement relative to the barrel to facilitate passage of at least a first component through the first plunger. A second plunger is disposed within the chamber. The second plunger includes at least one member configured for movement relative to the barrel to facilitate passage of at least a second component through the second plunger. In one embodiment, the second plunger may include an elastomeric element, such as an O-ring, X-ring, or square-cut around the perimeter of the second plunger, which forms a seal with the chamber.

In another embodiment, the first plunger includes a first disc, which is oriented substantially transverse to the longitudinal axis of the chamber to create a seal of a first section of the chamber. Positioning the first disc out of transverse relation to the longitudinal axis of the barrel facilitates passage of at least a first component through the first plunger. The size of the first section of the chamber may be varied depending upon the volume of the components to be mixed and the size of the first plunger, the first disc, and related components. When the first disc is positioned to create a seal of a first section of the chamber, the first disc is in its sealing configuration. When the first disc is in its sealing configuration, the first component is stored in isolation. When the first disc is not disposed in transverse orientation relative to the longitudinal axis of the barrel, the first disc is in its non-sealing configuration. In one embodiment, the first disc is removable. It is envisioned that the first disc may also assume its non-sealing configuration by orienting the first disc such that the first disc is not disposed in transverse orientation relative to the longitudinal axis of the barrel. When the first disc is in its non-sealing configuration, the first component, disposed in the first section of the chamber, may be mixed with other components in the chamber.

In one embodiment, the second plunger includes a removable second disc oriented substantially transverse to the longitudinal axis of the chamber to create a seal of a second section of the chamber. The size of the second section of the chamber may be varied depending upon the volume of the components to be mixed and the size of the second plunger, the second disc, and related components. When the second disc is oriented substantially transverse to the longitudinal axis of the chamber to create a seal of the second section of the chamber, the second disc is in its sealing configuration. When the first disc and the second disc are in their sealing configurations, the first component is stored in isolation within the first section of the chamber and the second component is stored in isolation within the second section of the chamber. Furthermore, the first disc and the second disc, in their sealing configurations, create a seal of a third section of the chamber, for disposal of a third component. The size of the third section of the chamber may be varied depending upon the volume of the components to be mixed. By providing three (3) isolated sections of the chamber, the multiple component mixing and delivery system can provide for the separation of at least three (3) components in a device which is suitable for storage, mixing, and subsequent delivery of the combined components.

When the first plunger is in its non-sealing configuration and the second disc is in its sealing configuration, the first component and the second component are permitted to mix. When the first plunger is in its non-sealing configuration and the second disc is in its sealing configuration, the mixture of the first component and the second component are stored in isolation within the space defined by first section of the chamber and the second section of the chamber.

When the second disc is not disposed in transverse orientation relative to the longitudinal axis of the barrel, the second disc is in its non-sealing configuration. In one embodiment, the first disc is removable. It is envisioned that the second disc may also assume its non-sealing configuration by orienting the second disc such that the second disc is not disposed in transverse orientation relative to the longitudinal axis of the barrel. When the second disc is in its non-sealing configuration, either the second component (if the first plunger is in its sealing configuration) or a mixture of the first component and the second component (if the first plunger is in its non-sealing configuration), are mixed with the component contained in the third section of the chamber.

In an alternative embodiment, a plunger rod extends from the first plunger and a second plunger rod extends from the second plunger, the first plunger rod and the second plunger rod being coaxial. The plunger rod extending from the first plunger acts to move the first plunger longitudinally within the chamber. The plunger rod extending from the second plunger acts to move the second plunger longitudinally within the chamber. In one particular embodiment, the first plunger has a tubular first plunger rod extending therefrom and the first disc is removable via the first plunger rod. In particular, the first plunger rod is moved opposite the proximal portion of the barrel in order to draw the first disc within the first plunger rod, thereby removing the first disc from the barrel. In another embodiment, the second plunger has a tubular second plunger rod extending therefrom and the second disc is removable via the tubular second plunger rod. In particular, the second plunger rod is moved opposite the proximal portion of the barrel in order to draw the second disc within the first plunger rod, thereby removing the second disc from the barrel.

In another embodiment, the first plunger further includes at least one member having a blade arrangement. The blade arrangement of the first plunger includes at least one (1) pivotable blade. When the pivotable blade or blades of the first plunger are in their initial, non-pivoted position, the pivotable blades of the first plunger are substantially parallel to the first plunger. In one particular embodiment, the first plunger, including its pivotable blades, is affixed to a tubular plunger rod of the first plunger, such that moving the plunger rod of the first plunger axially also moves the first plunger within the barrel.

To facilitate mixing of at least a first component and a second component, the pivotable blades of the first plunger are pivoted away from the first plunger and then reciprocated axially by moving the tubular plunger rod of the first plunger back and forth, which moves the first plunger, including the pivotable blades, longitudinally within the chamber. It is envisioned that the pivotable blades of the first plunger may be pivoted within a range of negative 90 degrees to 90 degrees relative to the first plunger. In one particular embodiment, the pivotable blades of the first plunger may be pivoted within a range of negative 45 degrees to 45 degrees relative to the first plunger.

In one embodiment, the second plunger further includes at least one member having a blade arrangement. The blade arrangement of the second plunger includes at least one pivotable blade. When the pivotable blade or blades of the second plunger are in their initial, non-pivoted position, the pivotable blades of the second plunger are substantially parallel to the second plunger. In one particular embodiment, the pivotable blades of the second plunger are affixed to a tubular plunger rod of the second plunger, such that moving the plunger rod of the second plunger axially also moves the second plunger within the barrel.

To facilitate mixing of at least a first component and a second component, the pivotable blades of the second plunger are pivoted away from the first plunger and then reciprocated axially by moving the tubular plunger rod of the second plunger back and forth, which moves the second plunger, including the pivotable blades, longitudinally within the chamber. It is envisioned that the pivotable blades of the second plunger may be pivoted within a range of negative 90 degrees to 90 degrees relative to the second plunger. In one particular embodiment, the pivotable blades of the second plunger may be pivoted within a range of negative 45 degrees to 45 degrees relative to the second plunger.

In another embodiment, the blade arrangement of the first plunger and the blade arrangement of the second plunger are releasably lockable, in order to lock the pivotable blade or blades of the first plunger and the pivotable blade or blades of the second plunger in their initial, non-pivoted positions, as well as to release the pivotable blade or blades of the first plunger and the pivotable blade or blades of the second plunger, which permits the blade arrangement to pivot relative to the longitudinal axis. In one particular embodiment, the blade arrangement of the first plunger and the blade arrangement of the second plunger include a locking pin, which is releasably lockable within a recess of the barrel proximate to the first and second plungers, respectively.

In another embodiment, the first plunger is movable between a first position and a second position. While in the first position, the member of the first plunger is oriented substantially transverse to the longitudinal axis, which prevents passage of at least a first component through the first plunger. While in the second position, the member of the first plunger is oriented at an angle of approximately 45 degrees to the longitudinal axis, which permits the passage of at least a first component through the first plunger. In one particular embodiment, the member of the first plunger is pivotable through an angle of approximately 120 degrees relative to the longitudinal axis.

In another embodiment, the second plunger is movable between a first position and a second position. While in the first position, the member of the second plunger is oriented substantially transverse to the longitudinal axis, which prevents the passage of material through the second plunger. In one particular embodiment, the member of the second plunger is releasably lockable in the first position. While in the second position, the member of the second plunger is oriented at an angle of approximately 45 degrees to the longitudinal axis, which permits for the passage of at least a second component through the second plunger. In one particular embodiment, the member of the second plunger is pivotable through an angle of approximately 120 degrees relative to the longitudinal axis.

When the first plunger is in the second position and the second plunger is in the first position, the first component and the second component are permitted to mix. The mixture of the first component and the second component are stored in isolation within the space defined by first section of the chamber and the second section of the chamber. When the second plunger is in the second position, either the second component (if the first plunger is in its second position) or a mixture of the first component and the second component (if the first plunger is in its first position), are mixed with components contained in the third section of the chamber.

In one embodiment, the member of the first plunger is pivotally mounted to provide for movement relative to the first plunger and the member of the second plunger is pivotally mounted to provide for movement relative to the second plunger.

The multiple component substance may include at least three components. The components may be liquid components, viscous components, pasty components and solid components, such as a powder. Moreover, the system is applicable to a wide range of applications for storing, mixing, and delivering a multiple component substance containing a plurality of components.

In another embodiment, in accordance with the principles of the present disclosure, a method of mixing multiple components for delivery to a site is provided. The method includes the steps of: providing a cartridge, similar to those described herein; removing the first disc; moving the first plunger relative to the barrel such that the at least one member is configured for movement relative to the first plunger to facilitate passage of the first component and the third component through the first plunger in a mixture of the first component and the third component; fixing the first plunger adjacent to a proximal portion of the barrel; removing the second disc; moving the second plunger relative to the barrel such that the at least one member of the second plunger is configured for movement relative to the second plunger to facilitate passage of the second component and the mixture of the first component and the third component through the second plunger in a mixture of the second component with the mixture of the first component and the third component; fixing the second plunger adjacent to the proximal portion of the barrel; and delivering the mixture of the second component with the mixture of the first component and the third component to the site.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments of the multiple component mixing and delivery system and methods of use disclosed are discussed in terms of cartridges for storing, mixing, and dispensing a multiple component mixture. In particular, the system includes a multiple component cartridge for storing, mixing and delivering multiple components for medical treatment, and has plungers with relatively movable members configured to facilitate mixing and delivery of a multiple component mixture. It is envisioned that the multiple component cartridge provides a single device for mixing two or more stored components that can be delivered during a medical procedure. It is further envisioned that the presently disclosed system may be employed with various medical and dental procedures and treatments, including diagnosis, therapeutics and surgical. It is contemplated that the system may be used during various surgical treatments including open surgery and minimally invasive procedures.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms “a,” “an,” and “the” include the plural, and reference to a particular numerical value includes at least that particular value, unless the context clearly dictates otherwise. Ranges may be expressed herein as from “about” or “approximately” one particular value and/or to “about” or “approximately” another particular value. Further, recitation of ranges of values herein are merely intended to serve as a shorthand method of referring individually to each separate value falling within the range, unless otherwise indicated herein, and each separate value is incorporated into the specification as if it were individually recited herein. When such a range is expressed, another embodiment includes from the one particular value and/or to the other particular value. Similarly, when values are expressed as approximations, by use of the antecedent “about,” it will be understood that the particular value forms another embodiment.

As used herein, “comprising,” “including,” “containing,” “characterized by,” and grammatical equivalents thereof are inclusive or open-ended terms that do not exclude additional, unrecited elements or method steps, but will also be understood to include the more restrictive terms “consisting of” and “consisting essentially of.”

Figure 1:
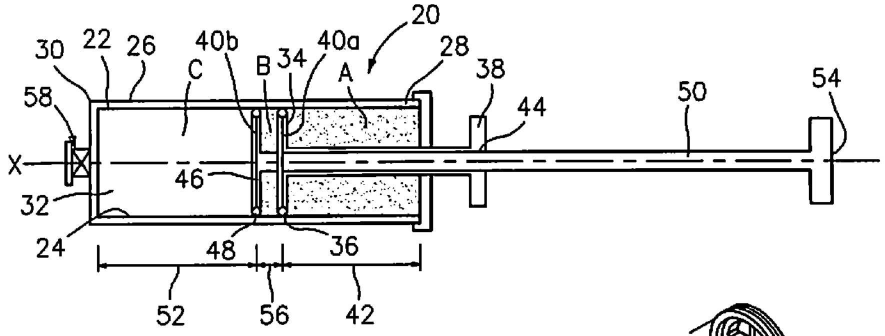
FIG. 1 is a side view of one particular embodiment of a multiple component mixing and delivery system in accordance with the principles of the present disclosure.
Figure 2:
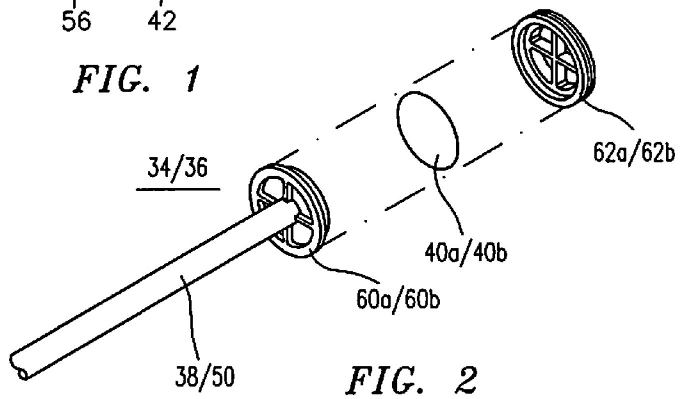
FIG. 2 is an exploded cutaway perspective view of a plunger of the multiple component mixing and delivery system shown in FIG. 1.
Figure 3:
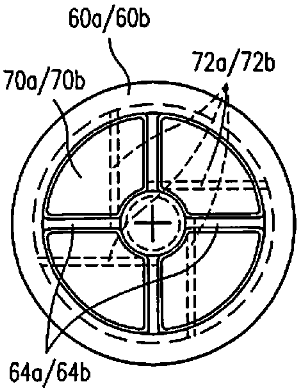
FIG. 3 is a plan view of a first part of the plunger shown in FIG. 2.
Figure 4:
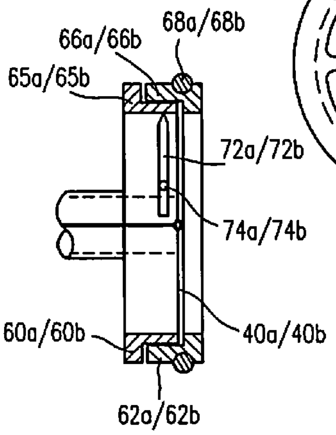
FIG. 4 is a side cross-section view of a portion of the plunger shown in FIG. 2.
Figure 5:
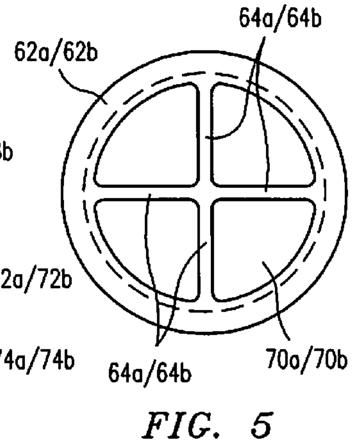
FIG. 5 is a plan view of a second part of the plunger shown in FIG. 2.
Figure 6:
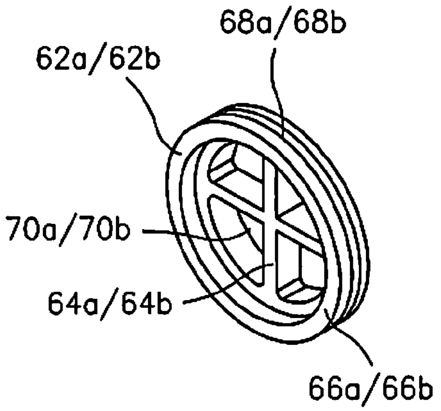
FIG. 6 is a perspective view of a second part of the plunger shown in FIG. 2.
Figure 7:
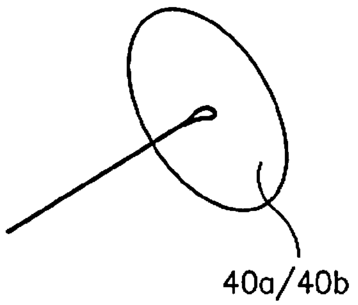
FIG. 7 is a perspective view of a disc of the multiple component mixing and delivery system shown in FIG. 1.
Figure 8:
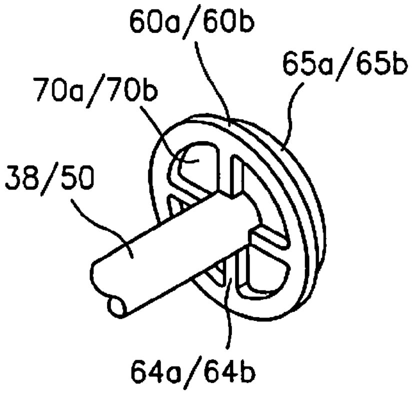
FIG. 8 is a perspective view of a portion of the plunger shown in FIG. 2.
Figure 9:
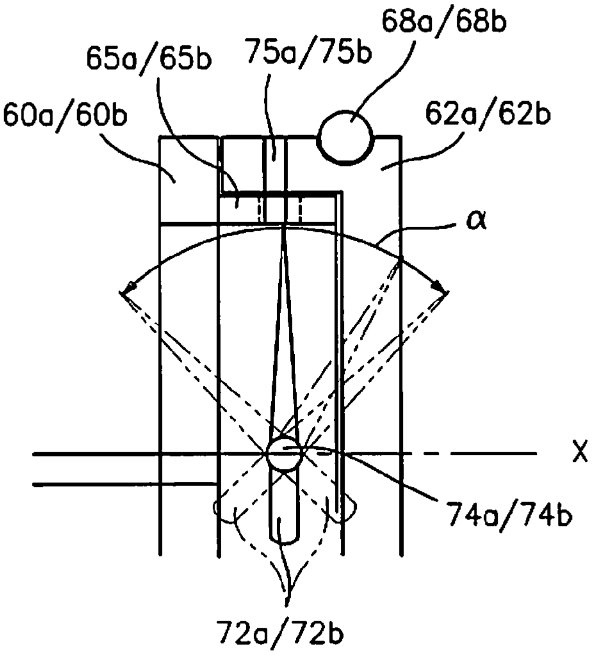
FIG. 9 is a side view of a portion of the plunger shown in FIG. 2 illustrating motion of a member of the plunger.
Figure 10:
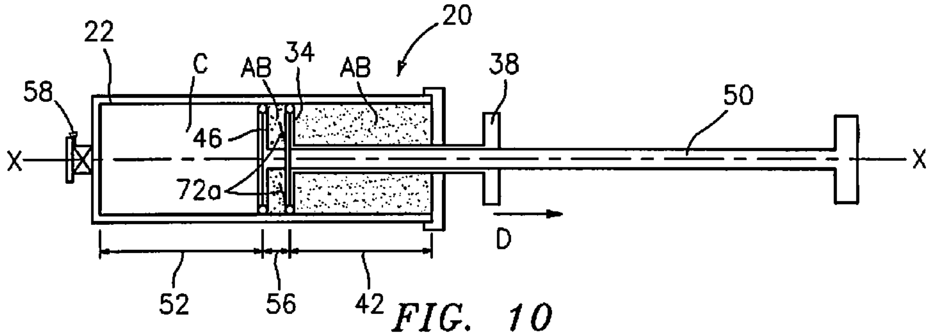
FIGS. 10-16 are side plan views of one particular embodiment of a method of use of the multiple component mixing and delivery system in accordance with the principles of the present disclosure.
Figure 11:
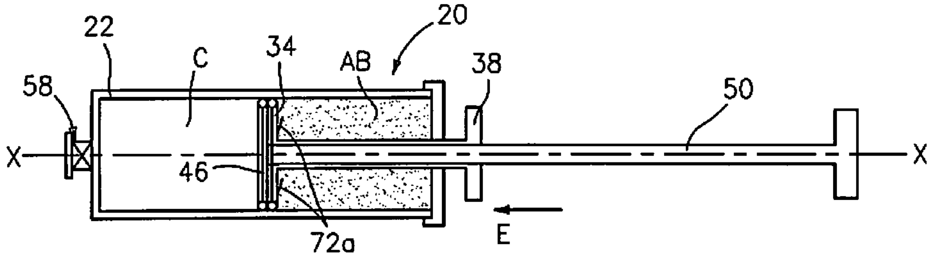

The following discussion includes a description of a multiple component mixing and delivery system, related components and exemplary methods of employing the multiple component mixing and delivery system in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated a multiple component cartridge 20 of a multiple component mixing and delivery system in accordance with the principles of the present disclosure.

The parts of multiple component cartridge 20 can be fabricated from materials suitable for medical applications, including metals, polymers, ceramics, biocompatible materials and/or their composites, and combinations thereof, depending on the particular application and/or preference of a medical practitioner. The parts may comprise a variety of materials, such as, for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The parts of multiple component cartridge 20 may include radiolucent and/or radio opaque materials.

Multiple component cartridge 20 includes a barrel 22 having an inner wall 24 and an outer wall 26 extending from a proximal portion 28 to a distal portion 30. It is contemplated that cartridge 20 may be employed with needles, cannulas, trocars, sheaths, minimally invasive instruments and other structure for medical applications. It is envisioned that barrel 22 can vary in length, cross section and geometry such as circular, elliptical and rectangular, according to the requirements of a particular application.

Barrel 22 defines a chamber 32 and a longitudinal axis x. It is envisioned that chamber 32 can vary in length, cross section and geometry such as circular, elliptical and rectangular, according to the requirements of a particular application. It is further envisioned that chamber 32 may be uniform, non-uniform or tapered in cross section and geometry. Barrel 22 includes a nozzle 58 defined adjacent distal portion 30. Nozzle 58 is configured to dispense a mixture of components, as will be described. Nozzle 58 may include a valve for delivering or discontinuing delivery of the mixture. The valve may provide a continuous or regulated flow, and may be electronically or processor controlled. It is envisioned that nozzle 58 be tapered or include a cap or clip structure for preventing flow. It is further envisioned that nozzle 58 may be configured as a luer lock, and/or for attachment with a needle or tubing.

A first plunger, such as, for example, a proximal plunger 34 is disposed within chamber 32. Proximal plunger 34 has an outer surface 36 disposed in sealing engagement with inner wall 24. Proximal plunger 34 is oriented substantially transverse to longitudinal axis x. It is envisioned that proximal plunger 34 may be angularly disposed relative to longitudinal axis x. Proximal plunger 34 has a tubular rod 38 oriented for axial manipulation of proximal plunger 34. It is envisioned that rod 38 may also facilitate rotational manipulation of proximal plunger 34. It is further envisioned that rod 38 may be electronically or processor controlled, as is known to one skilled in the art.

Proximal plunger 34 includes a first disc 40*a* disposable between a sealing and a non-sealing configuration. In the sealing configuration, first disc 40*a* is disposed in transverse orientation relative to longitudinal axis x and is configured to create a seal of a first section, such as, for example, a proximal section 42 of barrel 22. Proximal section 42 is configured for disposal of a first component, such as, for example, a polymer A. It is contemplated that polymer A includes biopolymers that include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. Proximal section 42 can vary in length, cross section and geometry according to the requirements of a particular application. Proximal section 42 may be uniform or non-uniform with the cross section and geometry of barrel 22.

In the non-sealing configuration, first disc 40*a* is removable from proximal plunger 34 via an elongated cavity 44 defined by tubular rod 38. First disc 40*a* is removable to unseal proximal section 42 and release polymer A for mixing with other components, as will be discussed. It is contemplated that first disc 40*a* may be alternatively removed from proximal plunger 34 such as exterior to rod 38. It is further contemplated that first disc 40*a* is manipulable to unseal proximal section 42 by for example, dissolving, puncturing, rupturing or otherwise breaking the sealing configuration of first disc 40*a* with an instrument.

A second plunger, such as, for example, a distal plunger 46 is disposed within chamber 32. Distal plunger 46 has an outer surface 48 disposed in sealing engagement with inner wall 24. Distal plunger 46 is oriented substantially transverse to longitudinal axis x. It is envisioned that distal plunger 46 may be angularly disposed relative to longitudinal axis x. Distal plunger 46 has a tubular rod 50 oriented for axial manipulation of distal plunger 46. It is envisioned that rod 50 may also facilitate rotational manipulation of distal plunger 46. It is further envisioned that rod 50 may be electronically or processor controlled, as is known to one skilled in the art. Rod 50 is co-axial with rod 38 and slidable within cavity 44.

Distal plunger 46 includes a second disc 40*b* disposable between a sealing and a non-sealing configuration. In the sealing configuration, second disc 40*b* is disposed in transverse orientation relative to longitudinal axis x and is configured to create a seal of a second section, such as, for example, a distal section 52 of barrel 22. Distal section 52 is configured for disposal of a second component, such as, for example, a hydrogel or other therapeutic material C. Suitable hydrogels include natural hydrogels, and those formed from polyvinyl alcohol, acrylamides such as polyacrylic acid and poly(acrylonitrile-acrylic acid), non-resorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof. Additional examples of materials include a flowable material such as bone cement; other therapeutic materials such as bone morphogenetic protein, hydroxyapatite, hydroxyapatite tricalcium phosphate, or an anti-microbial substance. Components can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. Distal section 52 can vary in length, cross section and geometry according to the requirements of a particular application. Distal section 52 may be uniform or non-uniform with the cross section and geometry of barrel 22.

In the non-sealing configuration, second disc 40*b* is removable from distal plunger 46 via an elongated cavity 54 defined by tubular rod 50. Second disc 40*b* is removable to unseal distal section 52 and release hydrogel C for mixing with other components, as will be discussed. It is contemplated that second disc 40*b* may be alternatively removed from distal plunger 46 such as exterior to rod 50. It is further contemplated that second disc 40*b* is manipulable to unseal distal section 52 by for example, dissolving, puncturing, rupturing or otherwise breaking the sealing configuration of second disc 40*b* with an instrument.

First disc 40*a* and second disc 40*b* also create a seal of a third section, such as, for example, a mid section 56 of barrel 22 for disposal of a third component, such as, for example, an initiator B. As persons of ordinary skill are aware, mPEG may be used as a plasticizer for PLGA, but other polymers/excipients may be used to achieve the same effect. mPEG imparts malleability to the resulting formulations. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof. Mid section 56 can vary in length, cross section and geometry according to the requirements of a particular application. Mid section 56 may be uniform or non-uniform with the cross section and geometry of barrel 22. Removal of first disc 40*a* and second disc 40*b* unseals mid section 56 and releases initiator B for mixing with other components, as will be discussed. First disc 40*a* and second disc 40*b* may be fabricated from surgical grade materials, biologically compatible materials, non-water soluble materials, or substances that are inert to the adjacent component to be placed within the chamber. Examples of suitable materials include, but are not limited to, metal such as stainless steel and titanium, nitinol, carbon composites, plastic polymers, rubber, silicone, polyurethane and polycarbonate. It will be appreciated that the disc may be made of any combination of metal, plastic, carbon composite, nitinol, or other material suitable for the intended purpose.

Referring to FIGS. 2-9, the components of proximal plunger 34 are described. FIGS. 2-9 are also employed for the description of distal plunger 46, which utilizes like reference numerals, as indicated below.

Proximal plunger 34 has a first part 60*a* configured for attachment with a second part 62*a*, with first disc 40*a* disposed therebetween. First part 60*a* interlocks with second part 62*a* to maintain first disc 40*a* in a sealing configuration. First part 60*a* has an inner flange 65*a* that fits with an outer lip 66*a* of second part 62*a*. First part 60*a* maintains the interlocked relationship with second part 62*a* after removal of first disc 40*a*, discussed above. Second part 62*a* includes an elastomeric O-ring 68*a*, which facilitates sealing engagement of proximal plunger 34 with inner wall 24. First part 60*a* is fixedly attached to rod 38.

First part 60*a* and second part 62*a* have a cylindrical disc design and include ribs 64*a* configured to facilitate flow and agitation for mixing of the components. Ribs 64*a* define equally sized wedge shaped openings 70*a* configured for passage and mixing of the components. It is contemplated that openings 70*a* may be alternatively sized and configured, such as circular, elliptical and rectangular. It is further contemplated that proximal plunger 34 may include one, none or a plurality of openings. The openings of first part 60*a* and second part 62*a*, or the individual openings, may be alternately or uniformly sized and configured.

Proximal plunger 34 includes members, such as, for example, blades 72*a*, which are configured for movement relative to proximal plunger 34. Blades 72*a* are pivotally movable relative to proximal plunger 34 via a pin hinge 74*a* mounted with second part 62*a*. Blades 72*a* are rotatable through an angle $\alpha$ relative to longitudinal axis x to facilitate passage and agitation for mixing of the components for creating a mixture. It is contemplated that angle $\alpha$ may be in a range of −90 to 90 degrees relative to longitudinal axis x. Preferably, angle $\alpha$ is in a range of −45 to 45 relative to longitudinal axis x.

Four blades 72*a* are equidistantly disposed about second part 62*a* and enclose a portion of openings 70*a*. Blades 72*a* each have a wedge shaped configuration to facilitate passage and agitation for mixing of the components. It is contemplated that blades 72*a* may be alternatively sized and configured, such as circular, elliptical and rectangular. It is further contemplated that proximal plunger 34 may include one, none or a plurality of blades 72*a*. Blades 72*a* have a planar surface and a tapered end portion. It is contemplated that blades 72*a* may have alternate surface configurations such as undulating, or include one or a plurality of openings defined in the surface.

Each of blades 72*a* are releasably lockable with proximal plunger 34 via a locking pin 75*a*. Pin 75*a* is slidable through first part 60*a* and second part 62*a* for engagement and disengagement with blade 72*a*. Desirably, pin 75*a* engages blade 72*a* in a locked position in the sealing configuration associated with first disc 40*a*. In the non-sealing configuration associated with first disc 40*a*, pin 75*a* disengages from blade 72*a* to release blade 72*a* and permit pivotal rotation of blade 72*a*, as described. It is contemplated that pin 72*a* may be removable through barrel 22. It is further contemplated that blades 72*a* may be releasably lockable via alternative structure such as each tip portion of blade 72*a* having a reduced thickness end initially formed with proximal plunger 34 and easily fractured and released in the non-sealing configuration.

Distal plunger 46 has a first part 60*b* configured for attachment with a second part 62*b*, with second disc 40*b* disposed therebetween. First part 60*b* interlocks with second part 62*b* to maintain second disc 40*b* in a sealing configuration. First part 60*b* has an inner flange 65*b* that fits with an outer lip 66*b* of second part 62*b*. First part 60*b* maintains the interlocked relationship with second part 62*b* after removal of second disc 40*b*, discussed above. Second part 62*b* includes an elastomeric O-ring 68*b*, which facilitates sealing engagement of distal plunger 46 with inner wall 24. First part 60*b* is fixedly attached to rod 50.

First part 60*b* and second part 62*b* have a cylindrical disc design and include ribs 64*b* configured to facilitate flow and agitation for mixing of the components. Ribs 64*b* define equally sized wedge shaped openings 70*b* configured for passage and mixing of the components. It is contemplated that openings 70*b* may be alternatively sized and configured, such as circular, elliptical and rectangular. It is further contemplated that distal plunger 46 may include one, none or a plurality of openings. The openings of first part 60*b* and second part 62*b*, or the individual openings, may be alternately or uniformly sized and configured.

Distal plunger 46 includes blades 72*b*, similar to blades 72*a* described above, which are configured for movement relative to distal plunger 46. Blades 72*b* are pivotally movable relative to distal plunger 46 via a pin hinge 74*b* mounted with second part 62*b*. Blades 72*b* are rotatable through an angle α relative to longitudinal axis x to facilitate passage and agitation for mixing of the components for creating a mixture. Each of blades 72*b* are releasably lockable with distal plunger 46 via a locking pin 75*b*, similar to locking pin 75*a* described above.

As described, first disc 40*a* and second disc 40*b* are removable to unseal proximal section 42, mid section 56 and distal section 52. Proximal plunger 34 is movable relative to barrel 22 such that blades 72*a* are configured for movement to facilitate flow and agitation for formation of a mixture of polymer A and initiator B. Distal plunger 46 is movable relative to barrel 22 such that blades 72*b* are configured for movement to facilitate flow and agitation for formation of a mixture of hydrogel C with the mixture of polymer A and initiator B. It is contemplated multiple component cartridge 20 may facilitate the storage, mixing and delivery of two or a plurality of components.

Referring to FIGS. 10-16, multiple component cartridge 20 of a multiple component mixing and delivery system is provided, similar to that discussed above, and employed with a method of mixing multiple components for delivery to a site (not shown). It is envisioned that multiple component cartridge 20 may be employed with various medical treatments including treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like. It is further envisioned that multiple component cartridge 20 may be employed with bone cement delivery applications, such as treatment with vertebroplasty, total joint replacements, tumor resections, spinal procedures such as discograms, nucleus augmentation, and nucleus replacement. Multiple component cartridge 20 and its constituent parts are sterilized and otherwise prepared for use and dispensing of the desired mixture of components. Proximal section 42, mid section 56 and distal section 52 are separately filled with desired components, which are maintained in isolation prior to mixing. For example, multiple component cartridge 20 is pre-loaded such that proximal section 42 is filled with polymer A, mid section 56 is filled with initiator B and distal section 52 is filled with hydrogel C.

First disc 40*a* and second disc 40*b* are in the sealing configuration, as described above. First collapsible sealing disc 40*a* is removed from proximal plunger 34 through rod 38 via pulling on a center suture tie connected thereto and extending from rod 38 and retracting disc 40*a* into plunger rod 38 to assume the non-sealing configuration. Releasable locking pin 74*a* is disengaged from blades 72*a*, as described above. Polymer A is permitted to flow from proximal section 42 and initiator B is permitted to flow from mid section 56. Rod 38 is manipulated, in the direction of arrows D and E shown in FIGS. 10 and 11, such that blades 72*a* pivot relative to proximal plunger 34 through angle α relative to longitudinal axis x to facilitate passage and agitation of polymer A and initiator B for mixing thereof for creating a mixture, as described above.

Figure 12:
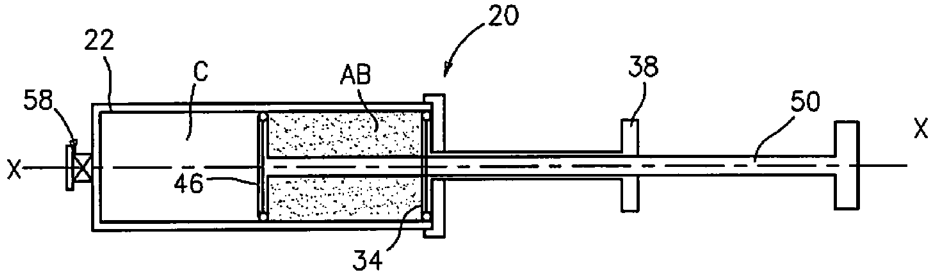
Figure 13:
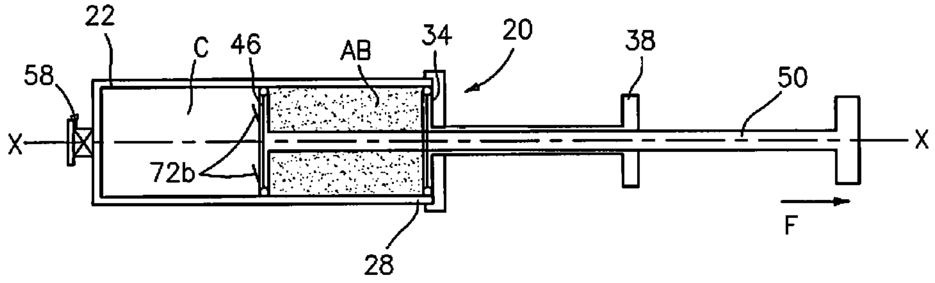
Figure 14:
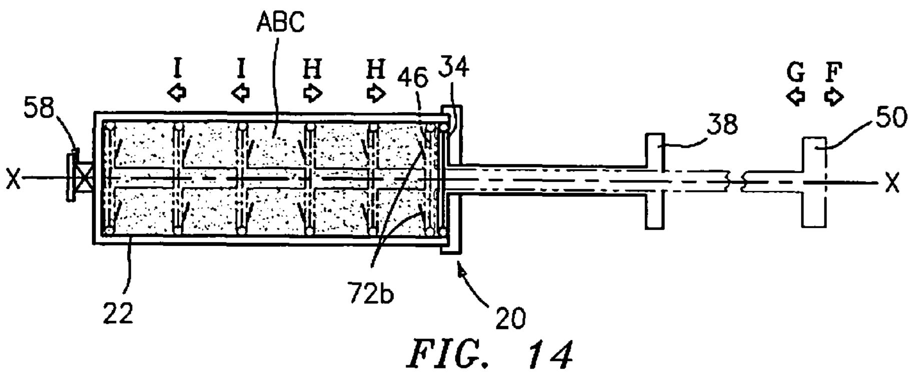

Rod 38 is manipulated such that proximal plunger 34 is locked adjacent to proximal portion 28 of barrel 22, as shown in FIG. 12. Rod 38 can be locked by various structure such as friction fit, detents, pins and clips.

Second collapsible sealing disc 40*b* is removed from distal plunger 46 through rod 50 via pulling on a center suture tie connected thereto and extending from rod 50 and retracting disc 40*b* into plunger rod 50 to assume the non-sealing configuration. Releasable locking pin 74*b* is disengaged from blades 72*b*. Rod 50 is manipulated, in the direction of arrow F shown in FIG. 13, such that blades 72*b* pivot relative to distal plunger 46 through angle α relative to longitudinal axis x to facilitate passage and flow of hydrogel C from distal section 52 into communication with the mixture of polymer A and initiator B. Rod 50 is further manipulated, in the direction of arrows F and G shown in FIG. 14, such that blades 72*b* pivot relative to distal plunger 46 through angle α relative to longitudinal axis x to facilitate passage and agitation of polymer A and initiator B, shown by arrows H and I, for mixing thereof for creating a mixture of polymer A, initiator B and hydrogel C, as described above.

Figure 15:
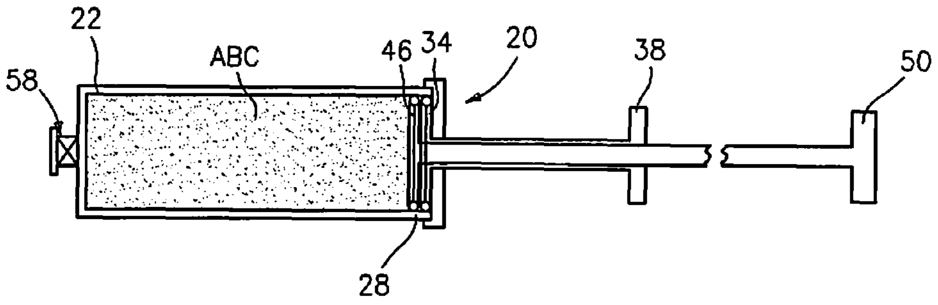
Figure 16:
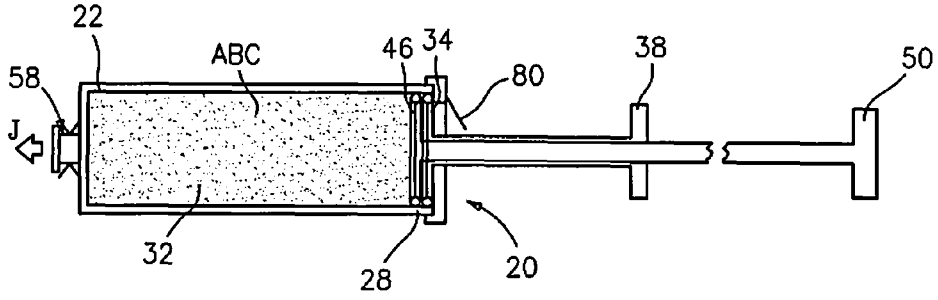

Rod 50 is manipulated such that distal plunger 46 is locked with proximal plunger 34, as shown in FIG. 15. Rod 50 can be manipulated to dispense the mixture of polymer A, initiator B and hydrogel C from chamber 32, in the direction shown by arrow J. A vent 80 is opened to relieve pressure from chamber 32. Nozzle 58 is opened and flow therefrom is regulated, as discussed above, such that the mixture of polymer A, initiator B and hydrogel C is delivered by injection to the site, as shown by arrow J in FIG. 16.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A multiple component cartridge comprising:

a barrel defining a chamber and a longitudinal axis;

a first plunger being disposed within the chamber and in sealing engagement with the barrel, the first plunger being movable relative to the barrel and including an elongated rod having a part connected to a distal end thereof, a surface of the part defining at least one opening and the part including at least one blade member connected thereto via a hinge pin that is perpendicular to an axis defined by said elongated rod, said at least one blade member being longitudinally aligned with at least a portion of the at least one opening such that the at least one blade member is configured for pivotal movement in a plane parallel to said axis defined by said elongated rod and in an axial direction relative to the surface of the part to facilitate passage of at least a first component through the first plunger; and a second plunger being disposed within the chamber and in sealing engagement with the barrel, the second plunger including at least one member and being movable relative to the barrel such that the at least one member of the second plunger is configured for movement relative to the second plunger to facilitate passage of at least a second component through the second plunger, wherein the first plunger includes a first disc configured to create a seal of a first section of the chamber for disposal of the first component, the first disc being manipulable to unseal the first section.

2. A multiple component cartridge according to claim 1, wherein the second plunger includes a second disc configured to create a seal of a second section of the chamber for disposal of the second component, the second disc being manipulable to unseal the second section.

3. A multiple component cartridge according to claim 2, the first disc and the second disc further creating a seal of a third section of the chamber for disposal of a third component, the first disc and the second disc being removable to unseal the sections of the chamber.

4. A multiple component cartridge according to claim 1, wherein the at least one member of the second plunger has a blade configuration.

5. A multiple component cartridge according to claim 1, wherein the first disc defines a plane oriented perpendicular to the longitudinal axis of the barrel, the first and second plunger being movable along the longitudinal axis, and wherein the first plunger is movable between a first position and a second position, in the first position the at least one blade member of the first plunger is oriented substantially parallel to the plane and in the second position the at least one blade member of the first plunger is oriented at an angle of approximately 45 degrees to the plane.

6. A multiple component cartridge according to claim 5, wherein the at least one member of the second plunger is movable between a first position and a second position, in the first position the at least one member of the second plunger is oriented substantially parallel to the plane and in the second position the at least one member of the second plunger is oriented at an angle of approximately 45 degrees to the plane.

7. A multiple component cartridge according to claim 1, wherein the at least one member of the second plunger is mounted for pivotable movement relative to the second plunger.

8. A multiple component cartridge according to claim 5, wherein the at least one member of the first plunger is releasably lockable in the first position.

9. A multiple component cartridge according to claim 6, wherein the at least one blade member of the first plunger and the at least one member of the second plunger are releasably lockable in the first position.

10. A multiple component cartridge according to claim 7, wherein the at least one blade member of the first plunger and the at least one member of the second plunger are each pivotable through an angle of 120 degrees relative to the plane.

11. A multiple component cartridge according to claim 1, wherein the rod of the first plunger is tubular and defines an elongated inner cavity, the first disc being configured for removal from the rod of the first plunger through the inner cavity to unseal the first section.

12. A multiple component cartridge according to claim 2, wherein the second plunger has a tubular second plunger rod extending therefrom that defines an elongated inner cavity, the second disc being configured for removal from the tubular second plunger rod through the inner cavity to unseal the second section.

13. A multiple component cartridge according to claim 1, wherein a part connected to a distal end of the second plunger rod, a surface of the part of the second plunger rod defining at least one opening and the part of the second plunger rod including the at least one member is connected thereto, which is longitudinally aligned with at least a portion of the at least one opening of the second plunger rod such that the at least one member of the second plunger rod is configured for pivotal movement relative to the surface of the part of the second plunger rod.

14. A multiple component cartridge according to claim 1, wherein the at least one blade member of the first plunger rod is releasably lockable with the part via a locking pin slidable through the part.

15. A multiple component cartridge according to claim 1, wherein a plunger rod extends from the first plunger and a second plunger rod extends from the second plunger, the first plunger rod and the second plunger rod being coaxial.

16. A multiple component cartridge comprising:

a barrel defining a chamber and a longitudinal axis;

a first plunger being disposed within the chamber and in sealing engagement with the barrel, the first plunger being movable relative to the barrel and including an elongated rod having a part connected to a distal end thereof, a surface of the part defining at least one opening and the part including at least one blade member connected thereto via a hinge pin that is perpendicular to an axis defined by said elongated rod, said at least one blade member being longitudinally aligned with at least a portion of the at least one opening such that the at least one blade member is configured for pivotal movement in a plane parallel to said axis defined by said elongated rod and in an axial direction relative to the surface of the part to facilitate passage of at least a first component through the first plunger; and a second plunger being disposed within the chamber and in sealing engagement with the barrel, the second plunger including at least one member and being movable relative to the barrel such that the at least one member of the second plunger is configured for movement relative to the second plunger to facilitate passage of at least a second component through the second plunger, wherein the first plunger includes a first disc configured to create a seal of a first section of the chamber for disposal of the first component, the first disc being manipulable to unseal the first section, and wherein the first disc defines a plane oriented perpendicular to the longitudinal axis of the barrel, the first and second plunger being movable along the longitudinal axis, and wherein the first plunger is movable between a first position and a second position, in the first position the at least one blade member of the first plunger is oriented substantially parallel to the plane and in the second position the at least one blade member of the first plunger is oriented at an angle of approximately 45 degrees to the plane.

* * * * *